(12) United States Patent
Kim et al.

(10) Patent No.: US 10,241,755 B2
(45) Date of Patent: Mar. 26, 2019

(54) METHOD AND APPARATUS FOR PHYSICAL EXERCISE ASSISTANCE

(71) Applicant: Samsung Electronics Co., Ltd., Gyeonggi-do (KR)

(72) Inventors: Jeong Yun Kim, Seoul (KR); Seung Seok Kang, Seoul (KR); Seok Hyun Kim, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 274 days.

(21) Appl. No.: 14/982,318

(22) Filed: Dec. 29, 2015

(65) Prior Publication Data

US 2016/0193502 A1 Jul. 7, 2016

(30) Foreign Application Priority Data

Jan. 6, 2015 (KR) .................. 10-2015-0001287

(51) Int. Cl.
| | | |
|---|---|---|
| *G06F 3/16* | (2006.01) | |
| *G06F 3/0488* | (2013.01) | |
| *G06F 19/00* | (2018.01) | |
| *G06F 3/01* | (2006.01) | |
| *G06F 3/0484* | (2013.01) | |
| *A63B 24/00* | (2006.01) | |

(52) U.S. Cl.
CPC .............. *G06F 3/167* (2013.01); *G06F 3/017* (2013.01); *G06F 3/0484* (2013.01); *G06F 3/0488* (2013.01); *G06F 19/00* (2013.01); *G06F 19/3481* (2013.01); *A63B 2024/0068* (2013.01)

(58) Field of Classification Search
None
See application file for complete search history.

(56) References Cited

U.S. PATENT DOCUMENTS

| | | | |
|---|---|---|---|
| 8,702,430 B2 | 4/2014 | Dibenedetto et al. | |
| 8,911,329 B2 | 12/2014 | Lin et al. | |
| 2009/0047645 A1 | 2/2009 | Dibenedetto et al. | |
| 2010/0060586 A1* | 3/2010 | Pisula ................. | G06F 3/04886 345/169 |
| 2012/0116550 A1* | 5/2012 | Hoffman ............ | A63B 24/0084 700/91 |
| 2013/0178335 A1 | 7/2013 | Lin et al. | |
| 2014/0092032 A1* | 4/2014 | Moore .................... | G06F 3/167 345/173 |
| 2014/0342329 A1 | 11/2014 | Debenedetto et al. | |
| 2016/0121161 A1* | 5/2016 | Mountain ........... | G06F 19/3481 482/4 |

FOREIGN PATENT DOCUMENTS

| | | |
|---|---|---|
| DE | 20 2013 000 110 U1 | 4/2013 |
| JP | 2005-224318 A | 8/2005 |
| JP | 2009-78134 A | 4/2009 |

* cited by examiner

*Primary Examiner* — Christopher J Fibbi
(74) *Attorney, Agent, or Firm* — Cha & Reiter, LLC

(57) ABSTRACT

An electronic device comprising: a memory; a display; and at least one processor configured to: control the display to display a lock screen including information provided by an exercise assisting application; detect an input performed while the lock screen is active; and generate a first audio signal indicating a value of an exercise parameter, in response to the input.

6 Claims, 10 Drawing Sheets

METHOD AND APPARATUS FOR PHYSICAL EXERCISE ASSISTANCE

CLAIM OF PRIORITY

This application claims the benefit under 35 U.S.C. § 119(a) of a Korean patent application filed on Jan. 6, 2015 in the Korean Intellectual Property Office and assigned Serial number 10-2015-0001287, the entire disclosure of which is hereby incorporated by reference.

TECHNICAL FIELD

The present disclosure relates to electronic devices, in general, and more particularly to a method and apparatus for physical exercise assistance.

BACKGROUND

With the trend of well-being, people who enjoy aerobic exercise to lose weight have recently increased. With this trend, electronic devices capable of measuring the amount of exercise of a user, such as electronic devices equipped with a GPS module, a heart rate sensor, a consumed calorie calculation module, a pedometer, or the like, have been developed.

In order to check the amount of exercise, a state of exercise, or relevant information through the above-mentioned electronic devices, such information should be visually checked from displays of the electronic devices.

However, in most cases, users who attempt to check the amount of exercise, the state of exercise, or the relevant information through the electronic devices are in the middle of a workout. Therefore, the users are required to temporarily stop working out and manipulate the electronic devices in order to check such information. The users' manipulation may interfere with continuous exercise and may prevent the users from concentrating on exercise.

SUMMARY

According to aspects of the disclosure, an electronic device is provided comprising: a memory; a display; and at least one processor configured to: control the display to display a lock screen including information provided by an exercise assisting application; detect an input performed while the lock screen is active; and generate a first audio signal indicating a value of an exercise parameter, in response to the input.

According to aspects of the disclosure, a method is provided comprising: displaying, by an electronic device, a lock screen including information provided by an exercise assisting application; detecting, by the electronic device, an input performed while the lock screen is active; and generating, by the electronic device, a first audio signal indicating a value of an exercise parameter, in response to the input.

A non-transitory computer-readable storage medium storing one or more programs comprising instructions which, when executed by at least one processor cause the at least one processor to execute a method comprising the steps of: displaying a lock screen including information provided by an exercise assisting application; detecting an input performed while the lock screen is active; and generating a first audio signal indicating a value of an exercise parameter, in response to the input.

DETAILED DESCRIPTION

Figure 1:
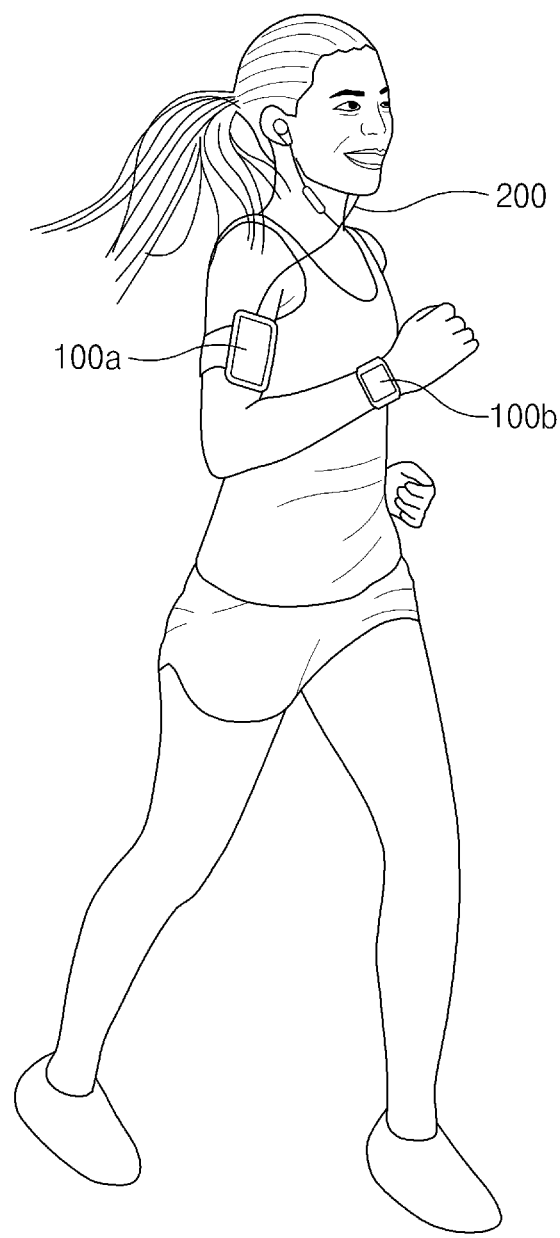
FIG. 1 is a diagram illustrating an example of the operation of an electronic device, according to an embodiment of the present disclosure is applicable.

Hereinafter, various embodiments of the present disclosure will be described in detail with reference to the accompanying drawings. However, it should be understood that the present disclosure is not limited to specific embodiments, but rather includes various modifications, equivalents, and alternatives of various embodiments of the present disclosure. Regarding the description of the drawings, like reference numerals may refer to like elements.

The term "have", "may have", "include", "may include" or "comprise" used herein indicates the existence of a corresponding feature (e.g., a number, a function, an operation, or an element) and does not exclude the existence of an additional feature.

The term "A or B", "at least one of A and/or B", or "one or more of A and/or B" may include all possible combinations of items listed together. For example, the term "A or B", "at least one of A and B", or "at least one of A or B" may indicate all the cases of (1) including at least one A, (2) including at least one B, and (3) including at least one A and at least one B.

The term "first", "second" or the like used herein may modify various elements regardless of the order and priority thereof, but does not limit the elements. For example, "a first user device" and "a second user device" may indicate different user devices regardless of the order or priority. For example, without departing the scope of the present disclosure, a first element may be referred to as a second element and vice versa.

It will be understood that when a certain element (e.g., a first element) is referred to as being "operatively or communicatively coupled with/to" or "connected to" another element (e.g., a second element), the certain element may be coupled to the other element directly or via another element (e.g., a third element). However, when a certain element (e.g., a first element) is referred to as being "directly coupled" or "directly connected" to another element (e.g., a second element), there may be no intervening element (e.g., a third element) between the element and the other element.

The term "configured (or set) to" may be interchangeably used with the term, for example, "suitable for", "having the capacity to", "designed to", "adapted to", "made to", or "capable of". The term "configured (or set) to" may not necessarily have the meaning of "specifically designed to". In some cases, the term "device configured to" may indicate that the device "may perform" together with other devices or components. For example, the term "processor configured (or set) to perform A, B, and C" may represent a dedicated processor (e.g., an embedded processor) for performing a corresponding operation, or a generic-purpose processor (e.g., a CPU or an application processor) for executing at least one software program stored in a memory device to perform a corresponding operation.

The terminology used herein is not for delimiting the present disclosure but for describing specific various embodiments. The terms of a singular form may include plural forms unless otherwise specified. The terms used herein, including technical or scientific terms, have the same meanings as understood by those skilled in the art. Commonly-used terms defined in a dictionary may be interpreted as having meanings that are the same as or similar to contextual meanings defined in the related art, and should not be interpreted in an idealized or overly formal sense unless otherwise defined explicitly. Depending on cases, even the terms defined herein should not be such interpreted as to exclude various embodiments of the present disclosure.

Hereinafter, an electronic device according to various embodiments of the present disclosure will be described with reference to the accompanying drawings. The term "user" used herein may refer to a person who uses an electronic device or may refer to a device (e.g., an artificial electronic device) that uses an electronic device.

FIG. 1 is a diagram illustrating an example of the operation of an electronic device, according to an embodiment of the present disclosure.

As illustrated, an electronic device according to an embodiment of the present disclosure may be attached to a body of a user and may assist the user in his or her exercise routine. For example, the electronic device may include a smartphone 100a or a smart watch 100b. For example, when the electronic device is the smartphone 100a, the electronic device may be attached to an arm of the user using an armband. As another example, when the electronic device is the smart watch 100b, the electronic device may be attached to a wrist of the user using a strap or a band.

The user wearing the electronic device according to various embodiments of the present disclosure may perform various exercises. For example, the user may perform various exercises such as basketball, soccer, football, tennis, rowing, jogging, hiking, walking, marathon, long-distance running, or the like. However, for the purposes of the present example, it will be assumed herein that the user performs a jogging.

In operation, the electronic device may generate an audio signal indicating an exercise state of the user in response to a certain input from the user or in a preset manner. The generated audio signal may be converted by an audio device (e.g., an earphone) 200 into an acoustic vibration so as to be provided to the user. For example, the audio device 200 may be implemented as an earphone, a headphone, or a Bluetooth earphone/headphone. The electronic device according to various embodiments of the present disclosure is not limited to the smartphone 100a or the smart watch 100b. For example, the electronic device may include any suitable type of electronic device, such as one or more of a tablet personal computer (PC), a mobile phone, a video telephone, an electronic book reader, a laptop PC, a netbook computer, a personal digital assistant (PDA), a portable multimedia player (PMP), an MP3 player, a mobile medical device, a camera, or a wearable device (e.g., smart glasses, a head-mounted-devices (HMD), an electronic apparel, an electronic bracelet, an electronic necklace, an electronic appcessory, an electronic tattoo, or a smart mirror).

According to various embodiments of the present disclosure, the electronic device may include one or more combinations of the above-mentioned devices. The electronic device according to some various embodiments of the present disclosure may include a flexible device. The electronic device according to an embodiment of the present disclosure is not limited to the above-mentioned examples, and may include new electronic devices with the development of technology.

Figure 2:
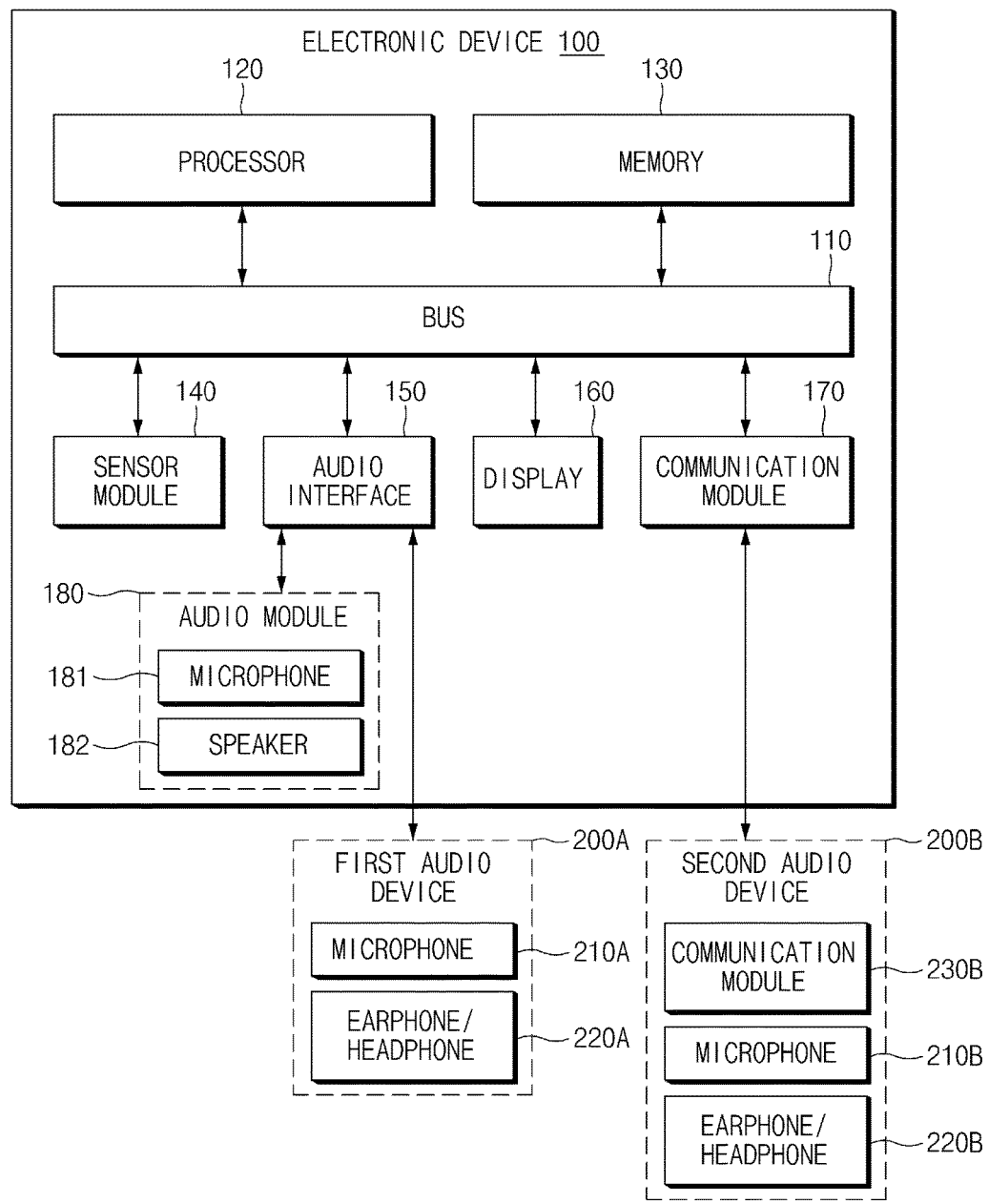
FIG. 2 is a diagram of an example of an electronic device, according to an embodiment of the present disclosure.

FIG. 2 is a diagram of an example of an electronic device, according to an embodiment of the present disclosure.

An electronic device 100 (e.g., the electronic device 100a or 100b) according to an embodiment of the present disclosure is described below with reference to FIG. 2. The electronic device 100 may include a bus 110, a processor 120, a memory 130, a sensor module 140, an audio interface 150, a display 160, and a communication interface 170. In some various embodiments of the present disclosure, at least one of the foregoing elements may be omitted or another element may be added to the electronic device 100. For example, an audio module 180 may be omitted from the electronic device 100 or may be installed therein.

The bus 110 may include a circuit for connecting the above-mentioned elements 120 to 170 to each other and transferring communications (e.g., control messages and/or data) among the above-mentioned elements.

The processor 120 may include any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), etc. In operation, the processor 120 may perform data processing or an operation for communication and/or control of at least one of the other elements of the electronic device 100.

The processor 120 may generate an audio signal indicating an exercise state of the user according to a user's input to a lock screen. The audio signal may be generated based on information obtained from an exercise assisting application (e.g., S-Health) that is being executed while the electronic device is locked.

The lock screen, which is maintained after the user has started exercising while the exercise assisting application is executed, may include any suitable type of lock screen, such as a standby screen unlock code entry screen, etc. For example, the lock screen may be displayed if no input from the user is detected by the electronic device 100 for a predetermined time after the start of the exercise of the user while the exercise assisting application is being executed. Furthermore, the lock screen may also be displayed in response to a power button of the electronic device 100 being pushed after the start of the exercise of the user while the exercise assisting application is executed.

Various applications such as the exercise assisting application, a music playback application, and the like may be executed in the background of the electronic device. In some implementations, while the lock screen is displayed, the display brightness of the electronic device may be decreased in order to reduce power consumption.

Figure 3:
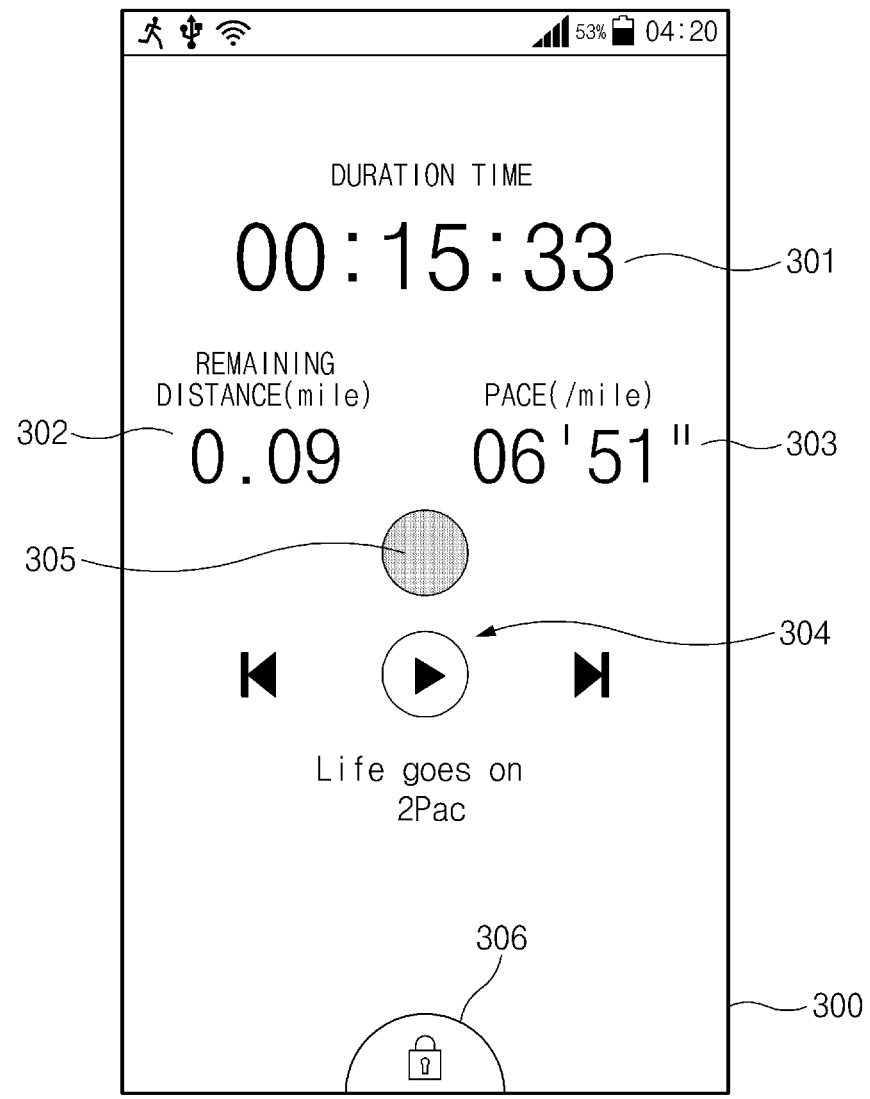
FIG. 3 is a diagram of an example of a lock screen, according to an embodiment of the present disclosure.

FIG. 3 is a diagram of an example of a lock screen, according to an embodiment of the present disclosure.

Referring to FIG. 3, a lock screen 300 including content generated (or otherwise provided) by one or more applications that are executed in the background of the electronic device (e.g., an exercise assisting application) may be displayed according to an embodiment of the present disclosure. For example, an object indicating exercise state information may be displayed on the lock screen 300. The object indicating the exercise state information may include an object 301 which indicates an exercise duration time, an object 302 for which indicates a remaining distance to a set destination, and an object 303 which indicates pace per mile. In some implementations, any of the objects may include an image, text, a number, and/or any other suitable type of content. Additionally or alternatively, the processor 120 may generate an audio signal indicating one or more of the exercise state corresponding to the items of the objects 301 to 303.

In addition, the lock screen 300 may display objects 304 corresponding to a music playback application and an object 306 for unlocking the lock screen. If the user does not execute the music playback application, the objects 304 may not be displayed.

Although FIG. 3 illustrates only three objects indicating the exercise state information, i.e., the objects 301 to 303, the number of the objects is not limited thereto. The objects 301 to 303 may be modified (added/replaced/removed) according to a user's setting (described below with reference to FIG. 4).

In some implementations, the electronic device 100 may receive a user input to the lock screen 300. The user input may include a touch to the lock screen 300. For example, if the user touches an arbitrary portion of the lock screen 300 that is associated with the exercise assisting application (excepting a portion on which the object 304 based on another application or the object 306 for unlocking the lock screen 300 is displayed), such as a touch portion 305 of FIG. 3, the processor 120 may generate the audio signal indicating an exercise state of the user.

In this manner, for example, the user may be provided with information on the exercise state of the user by touching an arbitrary portion of a display of the smartphone 100a without having to view the display, while jogging.

According to various embodiments of the present disclosure, the user input may include a voice input through a microphone (MIC). For example, if the user utters a preset voice command (e.g., "Tell me exercise state") while the exercise assisting application is executed (e.g., while the lock screen including content provided (e.g., generated) by the exercise assisting application is displayed), a microphone 181, 210A, or 210B of FIG. 2 may recognize the preset voice. Accordingly, the processor 120 may generate the audio signal indicating the exercise state of the user.

Figure 4:
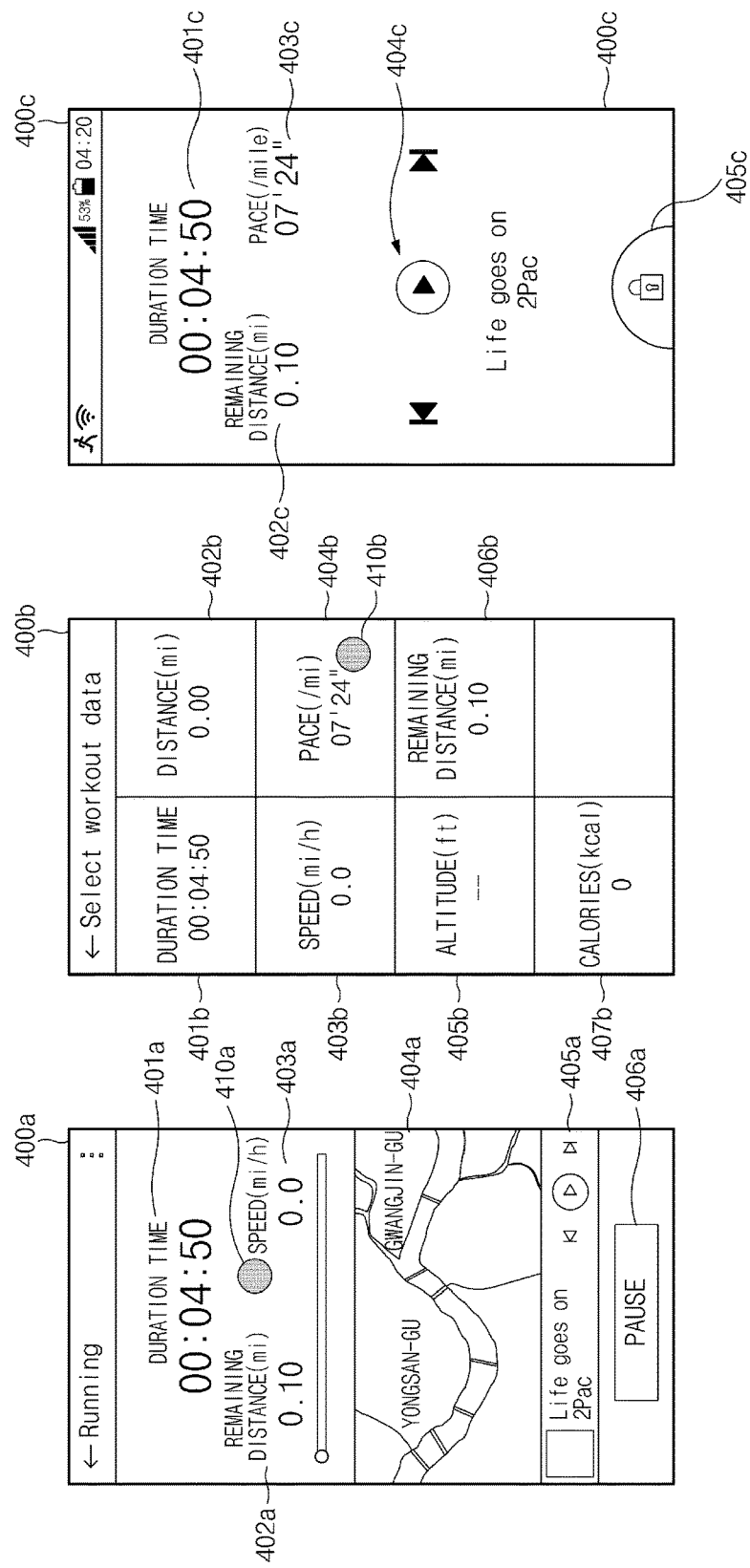
FIG. 4 is a diagram of an example of a user interface (UI), according to an embodiment of the present disclosure.

FIG. 4 is a diagram of an example of a user interface (UI), according to an embodiment of the present disclosure. More particularly, FIG. 4 illustrates a main screen 400a of the exercise assisting application. For example, the screen 400a may be displayed in response to a user selection of the object 306 for unlocking the lock screen of FIG. 3 while the user is exercising.

According to an embodiment of the present disclosure, the main screen 400a of the exercise assisting application may include objects for respective items of the exercise state, such as an object 401a which indicates an exercise duration time, an object 402a which indicates a remaining distance to a destination, and an object 403a which indicates a moving speed of the user. The objects 401a to 403a for the exercise state may correspond to the objects 301 to 303 of FIG. 3. As discussed above, each of the items of the exercise state may indicate the value of one or more exercise attributes of the user, such as speed, distance, etc.

Furthermore, the main screen 400a of the exercise assisting application may display an object 404a in which a current location of the user and a route from a departure point to a destination are mapped onto a map, an object 405a mapped by a music playback application, and an object 406a for starting/pausing the recording of exercise-related information.

The user may select an object for an exercise state item (e.g., the object 401a, 402a, or 403a) in order to change an exercise state item displayed on the main screen 400a of the exercise assisting application and/or the lock screen (e.g., the screen 300 of FIG. 3). For example, if the user desires to replace the item indicating the moving speed with another item that indicates another exercise attribute, the user may select the object 403a for the moving speed item by performing a touch 410a thereon. In response to the selection by the touch 410a, a screen 400b may be displayed on the display 160.

The screen 400b may include objects 401b to 407b corresponding to different exercise state items. As illustrated, the object 401b may indicate an exercise duration time, the object 402b may indicate a distance traveled by the user from a departure point, and the object 403b may indicate a moving speed of the user. Furthermore, the object 404b may indicate pace per mile, the object 405b may indicate an altitude of the user, the object 406b may indicate a distance to a destination, and the object 407b may indicate calories consumed after the user starts to exercise.

The user may select any one of the objects 401b to 407b in order to replace the item indicating the moving speed. For example, the user may select an item to be substituted by performing a touch 410b on the object 404b for the item indicating pace per mile. In response to the selection by the touch 410b, the object indicating the moving speed item may be replaced with the object indicating the user's pace per mile.

In this manner, although not shown in FIG. 4, an updated main screen of the exercise assisting application may display an object (corresponding to the object 401a of the screen 400a) for the item indicating the exercise duration time, an object (corresponding to the object 402a of the screen 400a) for the item indicating the distance to the destination, and an object indicating the user's pace.

After the object indicating the user's pace is selected from the screen 400b, a lock screen 400c may be displayed. The lock screen 400c may include the objects 401c to 403c which indicate the exercise state of the user. For example, the objects 401c, 402c, and 403c may respectively correspond to the objects 401b, 406b, and 404b displayed on the screen 400b.

In addition, for example, the lock screen 400c may display an object 404c (corresponding to the object 405a of the screen 400a) that is associated with a music playback application and an object 405c for unlocking the lock screen 400c.

As illustrated in FIG. 4, the exercise state items displayed on the lock screen may be changed with ease. The user may change the exercise state items displayed on the lock screen by selecting an object that is intuitive and has a relatively large area. Therefore, the user may perform the changing without interrupting the user's exercise.

Furthermore, according to an embodiment of the present disclosure, since an audio signal for providing the exercise state information may be generated based on the exercise state items displayed on the lock screen, the user may easily change, through simple manipulation, the exercise state information provided to the user.

According to an embodiment of the present disclosure, the processor 120 may analyze a reception pattern of a user input (e.g., a touch input or a voice input) to the lock screen, and may generate the audio signal at a time point (or timing) according to a result of analysis. Various analysis techniques such as machine learning or various pattern recognitions may be used to analyze a pattern of the user input.

As an example of pattern analysis, the processor 120 may calculate an audio notification period based on the timing of the user input to the electronic device. For example, it is assumed that the user who is jogging has touched the lock screen (or made a voice input) every three minutes over a certain period of time and has received the information on the exercise state in response to the touch (or voice input). In this case, the processor 120 may automatically set a notification period associated with the audio signal to three minutes. Afterwards, the processor 120 may automatically generate the audio signal containing the exercise state information every three minutes. In this manner, the user may receive the exercise state information automatically every three minutes without the user having to touch the lock screen.

As another example of pattern analysis, the processor 120 may calculate the audio notification period based on the moving speed of the user when the user input is received. For example, it is assumed that the user who is jogging has touched the lock screen (or made a voice input) every time the user's speed has fallen to about 6 km/h, during a certain period of time. In this case, the processor 120 may generate the audio signal containing the exercise state information every time the moving speed of the user reaches about 6 km/h. In this manner, the user may receive the exercise state information automatically every time the moving speed of the user reaches a certain threshold (or range), without the user having to touch the lock screen.

As another example of pattern analysis, the processor 120 may calculate the audio notification period based on the heart rate of the user when the user input is received. For example, it is assumed that the user who is jogging has touched the lock screen (or made a voice input) every time the heart rate of the user was 140 beats/minute over a certain period of time and has received the information on the exercise state in response to the touch (or voice input). In such instances, the processor 120 may generate an audio signal containing the exercise state information every time the heart rate of the user reaches 140 beats/minute. In this manner, the user may receive the exercise state information automatically every time the heart rate of the user reaches 140 beats/minute even if the user stops touching the lock screen.

Furthermore, according to an embodiment of the present disclosure, the processor 120 may monitor a preset exercise parameter, and may generate the audio signal indicating the exercise state of the user if a value of the preset exercise parameter reaches a predetermined threshold. The exercise parameter may include an exercise duration time, a moving distance, a moving speed, or consumed calories of the user. For example, it is assumed that the exercise parameter is the moving speed, and the predetermined value is 6 km. In this case, the processor 120 may monitor the moving speed, and may generate the audio signal indicating the exercise state of the user if the moving speed decreases (or increases) to 6 km.

Figure 5A:
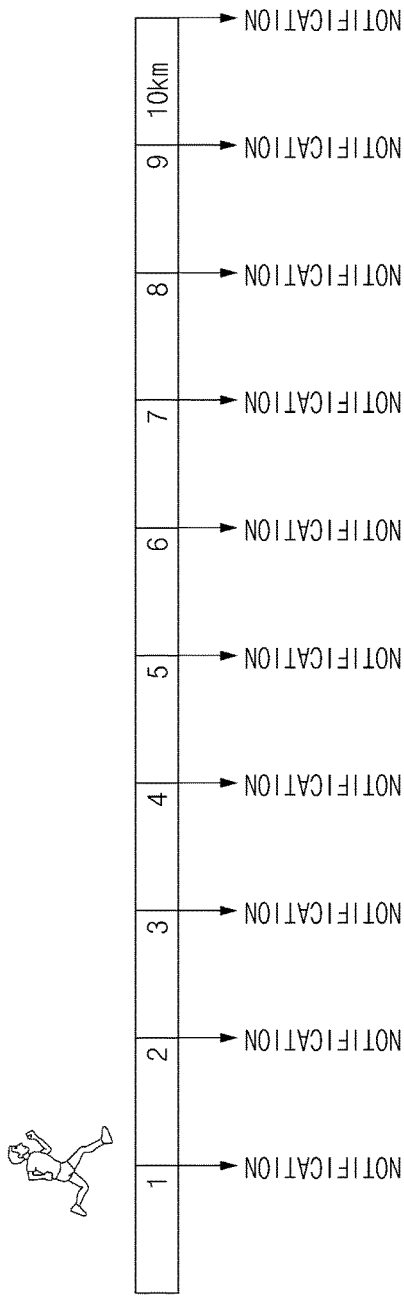
FIG. 5A is a diagram illustrating the operation of a process for outputting exercise state information, according to an embodiment of the present disclosure.
Figure 5B:
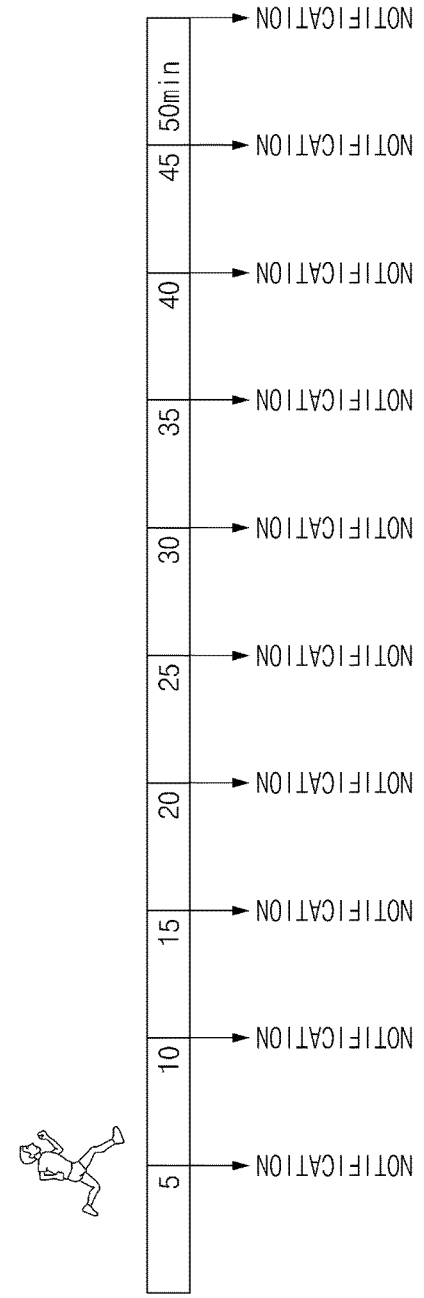
FIG. 5B is a diagram illustrating the operation of a process for outputting exercise state information, according to an embodiment of the present disclosure.
Figure 5C:
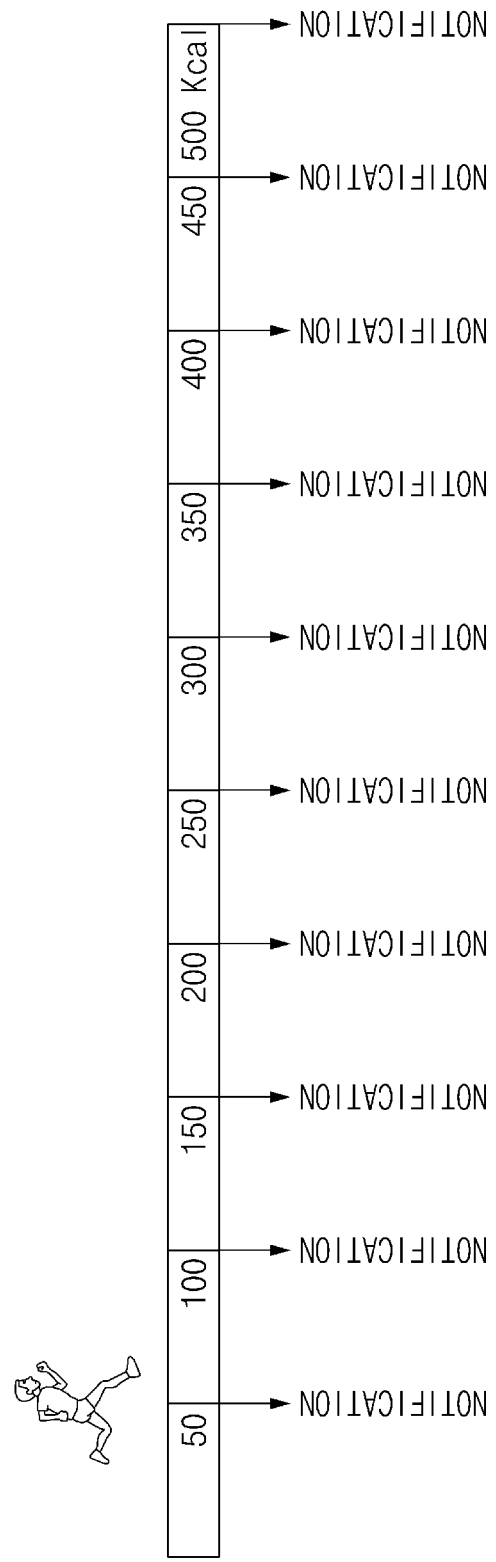
FIG. 5C is a diagram illustrating the operation of a process for outputting exercise state information, according to an embodiment of the present disclosure.

FIGS. 5A-C are diagrams illustrating the operation of different processes for outputting exercise state information, according to an embodiment of the present disclosure. According to the process, the processor 120 may monitor an exercise parameter value in real time based on information obtained from the sensor module 140 and/or the communication module 170 and generate an audio signal indicating the exercise state of the user in response to the exercise parameter value reaching a predetermined threshold (or one of a plurality of thresholds). As discussed above, the signal may indicate the values of one or more exercise attributes that at least in part constitute the exercise state of the user.

As illustrated in FIG. 5A, the user may set the exercise parameter as the user's moving distance (e.g., distance traveled by the user). If the user starts to jog or walk after setting the exercise parameter, the processor 120 may monitor the moving distance of the user in real-time based on location information obtained from a GPS module (e.g., may be included in the communication module 170). The processor 120 may generate the audio signal indicating the exercise state of the user every time the user travels by a distance of 1 km. As discussed above, the signal may indicate the values of one or more exercise attributes that at least in part constitute the exercise state of the user. Afterwards, the audio signal may be converted into an acoustic vibration through the audio module 180 or an audio device 200A or 200B and presented to the user.

As illustrated in the example of FIG. 5A, in some implementations, the processor 120 may determine a plurality of threshold values, such as 1, 2, . . . , 10 km. Thus, according to various embodiments of the present disclosure, a sequence of threshold values may be determined, wherein the values in the sequence are expected to be reached one after another by the user as the user goes through his or her exercise.

As illustrated in FIG. 5B, the user may set the exercise parameter as the user's exercise duration. If the user starts to exercise (e.g., jog), the processor 120 may monitor the exercise duration time of the user in real-time and generate the audio signal indicating the exercise state of the user after every five minutes of the user exercising. As discussed above, the signal may indicate the values of one or more exercise parameters that at least in part constitute the exercise state. The audio signal may be converted into an acoustic vibration through the audio module 180 or the audio device 200A or 200B and then may be provided to the user.

As illustrated in the example of FIG. 5B, the processor 120 may determine a plurality of threshold values, such as 5, 10, . . . , 50 minutes. Thus, according to various embodiments of the present disclosure, a sequence of threshold values may be determined, wherein the values in the sequence are expected to be reached one after another by the user as the user goes through his or her exercise.

As illustrated in FIG. 5C, the user may set the exercise parameter as consumed calories. For example, if the user starts to exercise (e.g., jog), the processor 120 may in real-time calculate and monitor the number of calories burned by the user while exercising, based on time information, location information (i.e., moving distance information), altitude information, heart rate information, and/or body composition information of the user pre-stored in the memory 130. The processor 120 may generate the audio signal indicating the exercise state of the user every time the user burns 50 kcal. The audio signal may be converted into an acoustic vibration through the audio module 180 or the audio device 200A or 200B and then may be provided to the user.

As illustrated in FIG. 5C, the processor 120 may determine a plurality of threshold values, such as 50, 100, . . . , 599 km. Thus, according to various embodiments of the present disclosure, a sequence of threshold values may be determined, wherein the values in the sequence are expected to be reached one after another by the user as the user goes through his or her exercise.

Meanwhile, in FIGS. 5A to 5C, the audio signal indicating the exercise state (i.e., exercise state information acoustically provided to the user) generated by the processor 120 may vary with the exercise parameter. An example of the exercise state information that may be differently provided to the user according to the exercise parameter is shown in Table 1 below.

TABLE 1

| Exercise parameter | Moving distance | Exercise duration time | Consumed calories |
|---|---|---|---|
| Exercise state information | (Alarm sound) Moving distance (Alarm sound) Exercise duration time (Alarm sound) Remaining distance to destination (Alarm sound) Average speed for each interval (Alarm sound) Estimated arrival time | (Alarm sound) Moving distance (Alarm sound) Exercise duration time (Alarm sound) Remaining distance to destination | (Alarm sound) Moving distance (Alarm sound) Exercise duration time (Alarm sound) Consumed calories (Alarm sound) Calories to be consumed to arrive at target calories (Alarm sound) Remaining distance for consuming target calories |

As shown in Table 1, the processor 120 may generate an audio signal corresponding to a given exercise parameter, and may thus provide optimal exercise state information to the user. For example, the audio signal may help the user to determine whether the user's pace gradually decreases or the user has run enough to consume a target number of calories.

Furthermore, in regard to provision of a plurality of exercise state information as shown in Table 1, the processor 120 may insert an alarm sound into the audio signals that identify the exercise attributes whose values are being presented. In some implementations, a different alarm sound may be associated with each of the exercise parameter. Accordingly, the user may clearly recognize the type of exercise state information that is being provided based on the alarm sounds.

Figure 6:
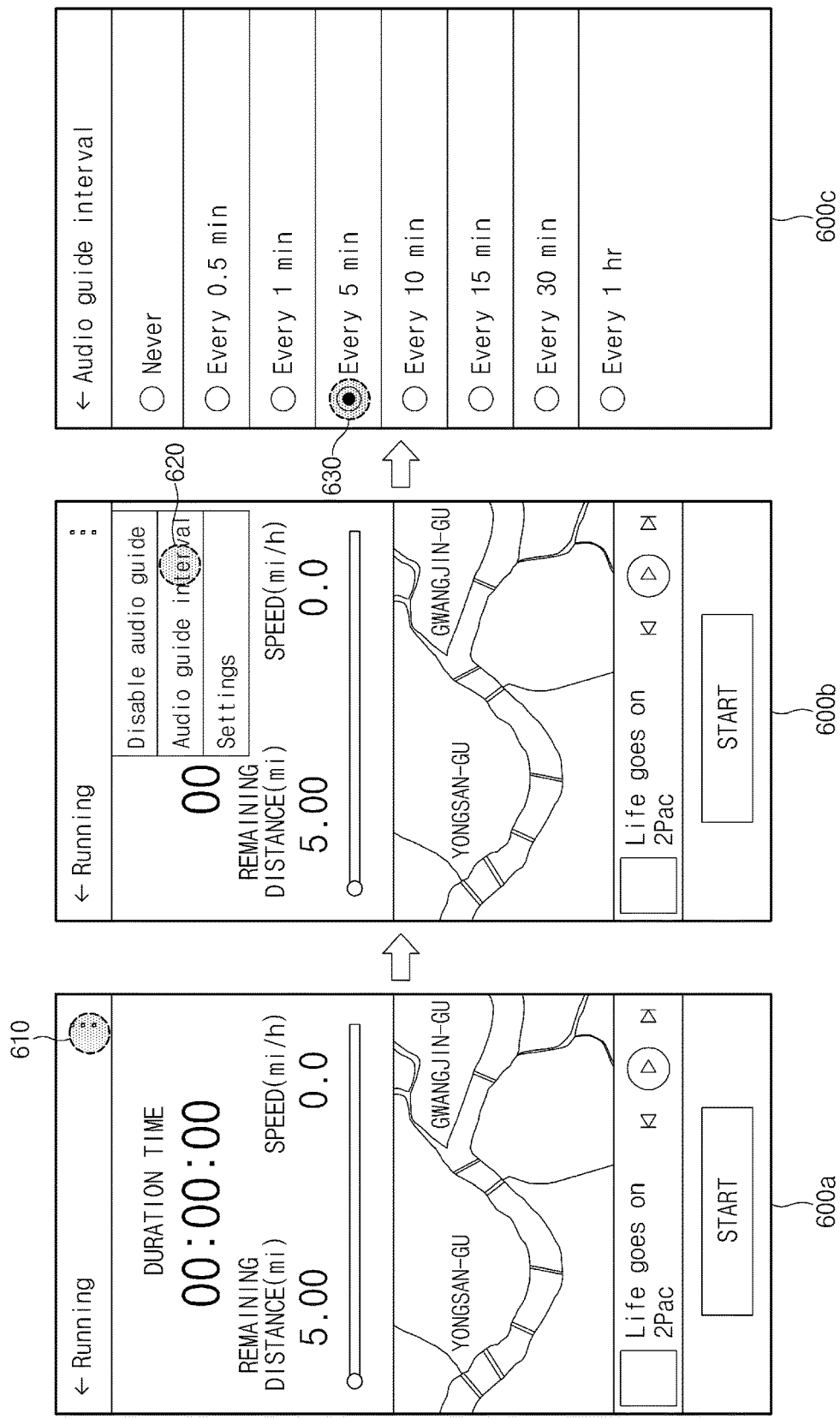
FIG. 6 is a diagram of an example of a user interface (UI), according to an embodiment of the present disclosure.

FIG. 6 is a diagram of an example of a user interface (UI), according to an embodiment of the present disclosure.

FIG. 6 illustrates screens 600a to 600c for setting a notification period when the exercise parameter is exercise duration (e.g., as illustrated in the example of FIG. 5A). The screen 600a may be the main screen of the exercise assisting application. In the screen 600a, the user may select an object displayed on an upper right end portion by performing a touch 610 thereon in order to specify the notification period. Once the touch 610 is performed, a popup window may be displayed on an upper right portion of the screen 600b, and the user may perform a touch 620 on a tab ("Audio guide interval" tab) for setting the notification period. Once the touch 620 is performed, the screen 600b may be switched to the screen 600c. The screen 600c displays a list of various notification periods. If the user desires to receive exercise state information every five minutes, the user may set the notification period to five minutes by performing a touch 630 on "Every 5 min" tab.

The notification period may correspond to a period of generating, by the processor 120, the audio signal indicating the exercise state. Alternatively, the audio signal may correspond to a period of converting, by the audio module 180 or the audio device 200A or 200B, the audio signal into an acoustic vibration.

Referring back to FIG. 2, the memory 130 may store the exercise assisting application and various execution information corresponding thereto. The memory 130 may include any suitable type of volatile or non-volatile memory, such as Random-access Memory (RAM), Read-Only Memory (ROM), Network Accessible Storage (NAS), cloud storage, a Solid State Drive (SSD), etc. In operation, the memory 130 may store instructions or data related to at least one of the other elements of the electronic device 100.

The sensor module 140 may measure a physical quantity or detect an operation state of the electronic device 100 so as to convert measured or detected information into an electric signal. For example, the electric signal obtained through conversion may be provided to the processor 120.

The sensor module 140 may include a barometric sensor for detecting an altitude, a magnetic sensor for detecting a direction and a location, an acceleration sensor for measuring an acceleration/speed, and a heart rate sensor for measuring a heart rate. The sensor module 140 is not limited to the foregoing examples. For example, the sensor module 140 may include at least one of a gesture sensor, a gyro sensor, a grip sensor, a proximity sensor, a color sensor (e.g., a red/green/blue (RGB) sensor), a biometric sensor, a temperature/humidity sensor, an illumination sensor, or an ultraviolet (UV) sensor. Additionally or alternatively, the sensor module 140 may include, for example, an olfactory sensor (E-nose sensor), an electromyography (EMG) sensor, an electroencephalogram (EEG) sensor, an electrocardiogram (ECG) sensor, an infrared (IR) sensor, an iris recognition sensor, and/or a fingerprint sensor.

The audio interface 150, through which an audio signal is transferred in the electronic device 100, may be connected to the audio module 180 or the first audio device 200A. For example, the audio signal generated by the processor 120 may be transmitted to a speaker 182 of the audio module 180 or an earphone/headphone 220A of the first audio device 200A via the audio interface 150. The speaker 182 or the earphone/headphone 220A may receive the audio signal, may convert the audio signal into an acoustic vibration, and may acoustically provide the acoustic vibration to the user.

Furthermore, the microphone 181 of the audio module 180 or the microphone 210A of the first audio device 200A may receive a voice from the user. The received voice may be converted into an electric signal, and then may be provided to the processor 120 via the audio interface 150. In this manner, the user may use the voice thereof as a user input.

The display 160 may present various content (e.g., a text, an image, a video, an icon, a symbol, or the like) to the user. For example, the display 160 may display the lock screen based on the exercise assisting application. The lock screen may display at least one item of the exercise state of the user.

The display 160 may include a touchscreen, and may receive a touch, gesture, proximity or hovering input from an electronic pen or a part of a body of the user. The display 160 may include, for example, a liquid crystal display (LCD), a light-emitting diode (LED) display, an organic light-emitting diode (OLED) display, a microelectromechanical systems (MEMS) display, or an electronic paper display.

The communication module 170 may include, for example, at least one of a cellular module, a Wi-Fi module, a Bluetooth module, a GPS module, an NFC module, or a radio frequency (RF) module.

Location information of the electronic device 100 may be received from a GPS satellite (not shown) via the communication module 170 (e.g., a GPS module). Furthermore, the communication module 170 (e.g., a Bluetooth module) may transmit the audio signal generated by the processor 120 to the second audio device 200B (or an earphone/headphone 220B thereof) by communicating with a communication module 230B of the second audio device 200B. Moreover, the communication module 170 may receive a voice signal from the user via the microphone 210B of the second audio device 200B and the communication module 230B. The received voice may be provided to the processor 120 via the bus 110.

Figure 7:
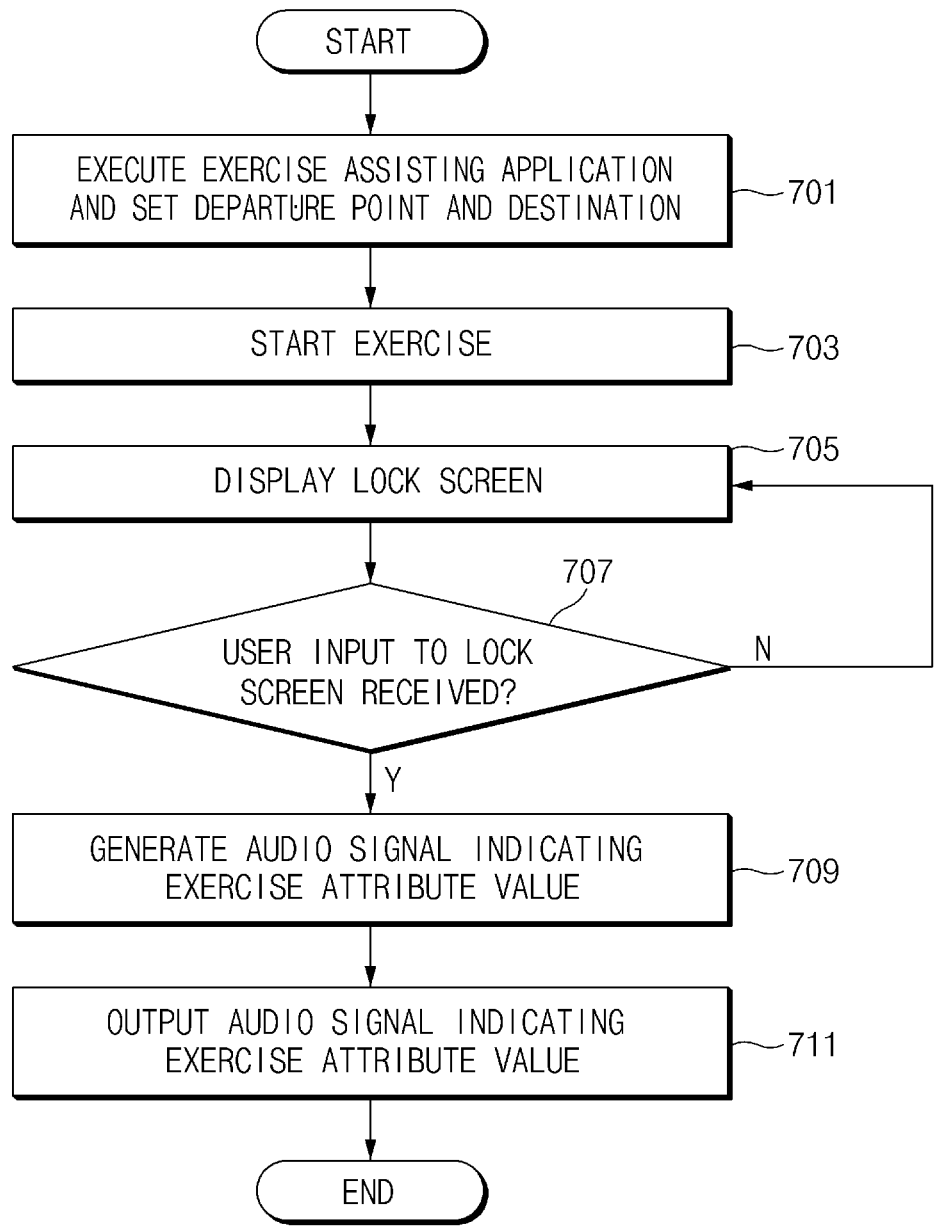
FIG. 7 is a flowchart of an example of a process, according to an embodiment of the present disclosure.

FIG. 7 is a flowchart of an example of a process, according to an embodiment of the present disclosure.

In the example of FIG. 7, a user jogs from a departure point to a destination, such that while the user is jogging, the user is provided with exercise state information.

In operation 701, the exercise assisting application stored in the electronic device 100 may be executed in response to a user input. Furthermore, the departure point and the destination of the exercise may be specified in the exercise assisting application via further user input.

In operation 703, the user begins exercising, and the electronic devices begins to monitor the user's exercise.

In operation 705, if the power button of the electronic device 100 is pushed or no user input is detected for a predetermined period, the electronic device 100 may display the lock screen including information provided (e.g., generated) by the exercise assisting application. The lock screen may display at least one of a plurality of exercise state items. Each of the exercise state items may include an indication of the value of a given exercise attribute. For example, the plurality of exercise state items may indicate one or more of exercise duration time, a moving distance, an altitude, a moving speed, distance to a destination, consumed calories, or time taken by the user to jog a certain distance.

In operation 707, the electronic device 100 may determine whether a user input is received. The user input to the lock screen may include a touch input to at least a part of the lock screen or a voice command provided through a microphone while the lock screen is displayed and/or the electronic device 101 is locked. If the user input is received, the process may proceed to operation 709, or, if the user input is not received, the process may return to operation 705.

In operation 709, when the electronic device 100 receives the user input (e.g., to the lock screen), the electronic device 100 may generate an audio signal indicating the value of an exercise attribute associated with the user. By way of example, the signal may indicate the value of one or more of exercise duration time, a moving distance, an altitude, a moving speed, distance to a destination, consumed calories, or time taken by the user to travel a certain distance.

In operation 711, the electronic device 100 or the audio device 200A or 200B connected to the electronic device 100 may convert the audio signal generated in operation 709 into an acoustic vibration and may provide the acoustic vibration to the user. Accordingly, the user may be acoustically provided with exercise state information contained in the audio signal.

According to the exercise assisting method according to an embodiment of the present disclosure, the user who is exercising may be acoustically provided with information on the exercise state of the user by providing a simple user input to the lock screen. Therefore, may permit the user to better concentrate on exercising while receiving the exercise state information.

Figure 8:
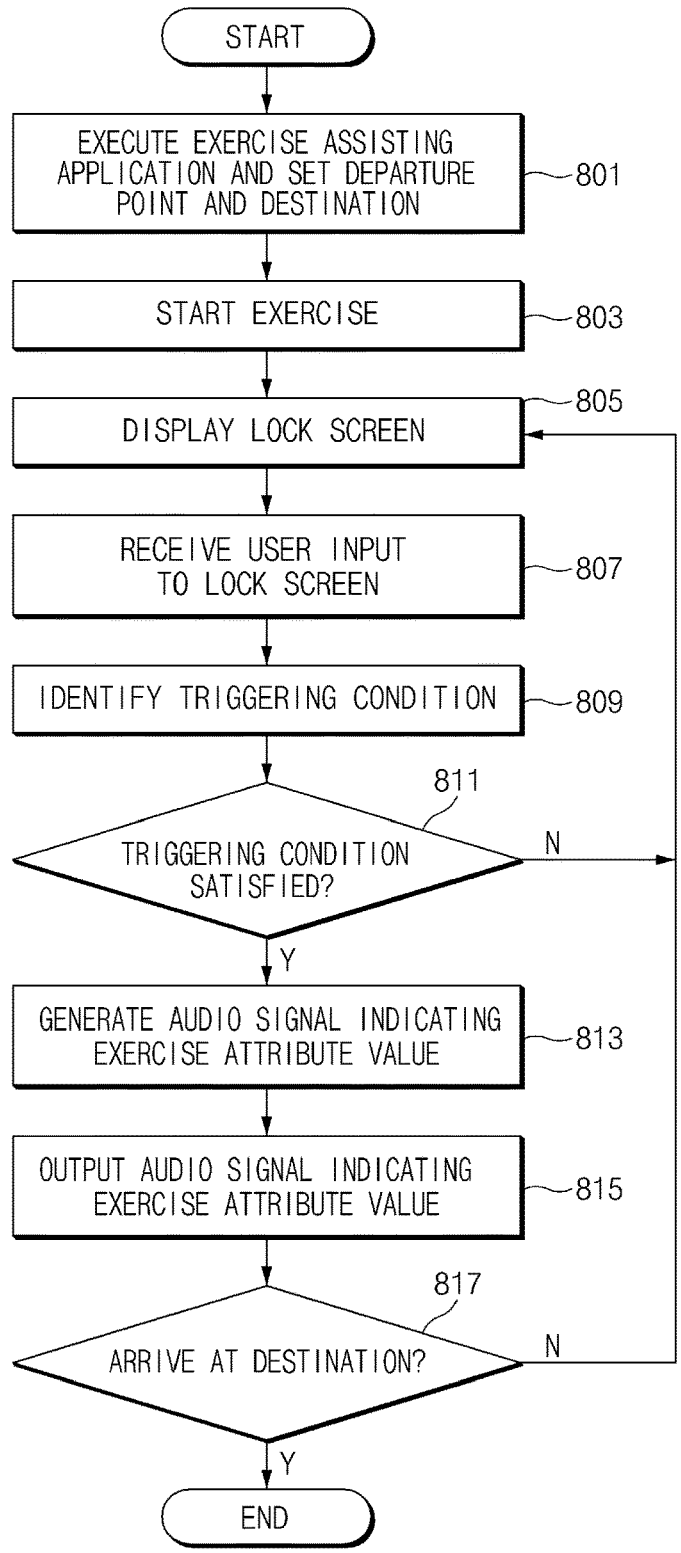
FIG. 8 is a flowchart of an example of a process, according to an embodiment of the present disclosure.

FIG. 8 is a flowchart of an example of a process, according to an embodiment of the present disclosure.

In the example of FIG. 8, operations 801, 803, 805, 813, and 815 are identical to operations 701, 703, 705, 709, and 711 of FIG. 7, respectively, and, therefore, a detailed description of these operations will be omitted.

In operation 807, the electronic device 100 may receive a user input to the lock screen which is displayed by the electronic device. If the user input is received, the electronic device 100 may generate an audio signal indicating an exercise state in response to the user input in operation 813.

In operation 809, the electronic device 100 may analyze a pattern of the received user input, and may calculate a triggering condition for the automatic output of exercise state information based on the outcome of the analysis. In regard to the analysis of the pattern of the user input, the electronic device 100 may analyze a reception pattern of the user input based on a time, a pattern of the moving speed of the user at the moment of receiving the user input, or a pattern of the heart rate of the user at the moment of receiving the user input. Thus, as discussed above, the triggering condition may be determined based on the time when the user input is detected, the speed of the user when the user input is detected, and/or the heart rate of the user when the user input is detected. Operations 809 and 813 may be performed at the same time or at different times.

In operation 811, the electronic device 100 may determine whether the triggering condition is satisfied. If the electronic device 100 determines that the triggering condition identified as a result of the analysis is satisfied, the process may proceed to operation 813 so that the electronic device 100 may automatically generate and output the audio signal indicating the exercise state at operations 813 and 815. However, if it is determined that the triggering condition is not satisfied, the process may return to operation 805.

In operation 817, the electronic device 100 may determine whether the user arrives at the destination based on the location information. If the user arrives at the destination, the process may be terminated, or, if the user does not arrive at the destination, the process may return to operation 805. In the case where the process is terminated as the user arrives at the destination, the electronic device 100 may display, on the display 160, a normal lock screen to which the exercise assisting application is not mapped. Thus, in some implementations, the lock screen displayed on the electronic device may be varied depending on whether the user has accomplished a particular exercise goal (e.g., arriving at a specified destination, etc.)

According to the exercise assisting method based on pattern analysis according to an embodiment of the present disclosure, the user may be provided with the exercise state information according to the result of the analysis even if the user input to the lock screen is stopped. Since the pattern analysis is based on a habit or a biometric state of the user, the user may be provided with the exercise state information at an intended time.

Figure 9:
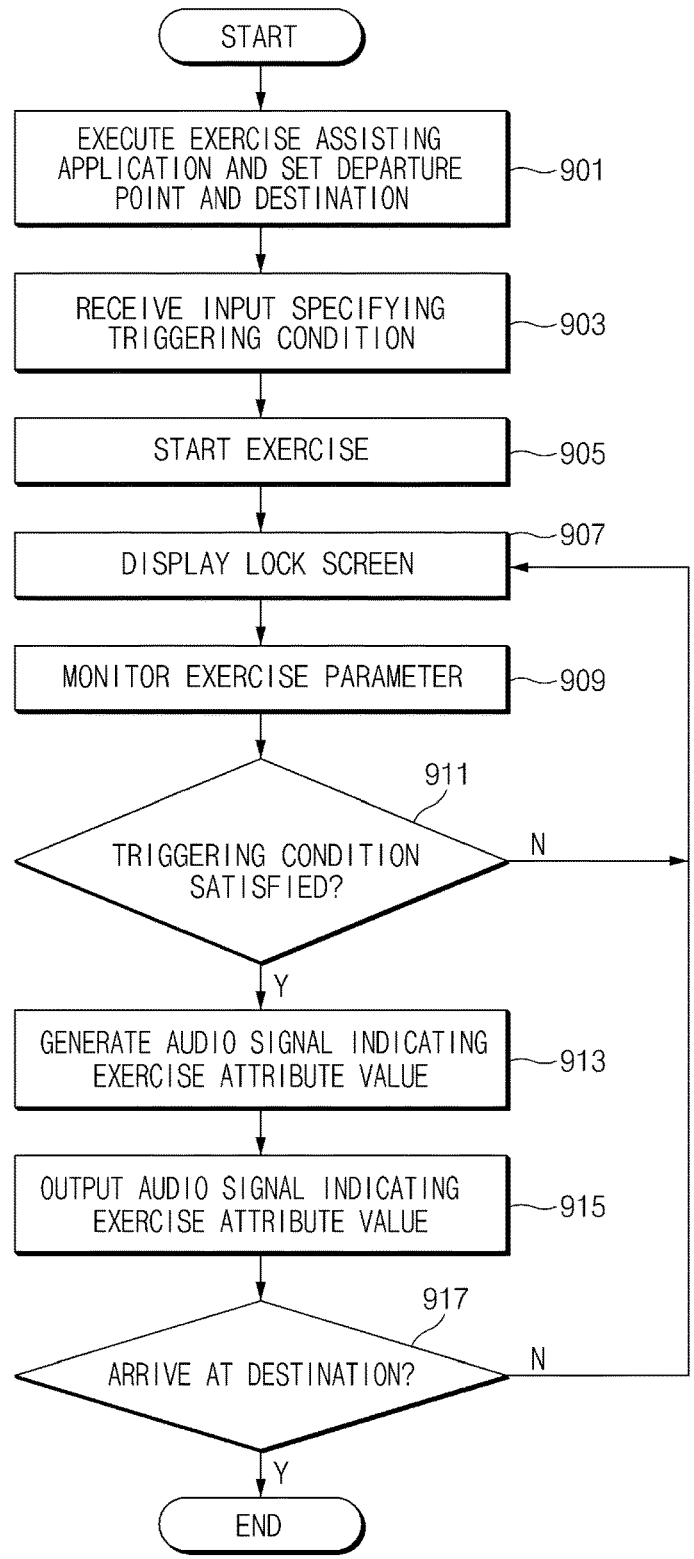
FIG. 9 is a flowchart of an example of a process, according to an embodiment of the present disclosure.

FIG. 9 is a flowchart of an example of a process, according to an embodiment of the present disclosure.

Referring to FIG. 9, the exercise assisting method based on an exercise parameter according to an embodiment of the present disclosure may include operations 901 to 917. Since operations 901, 905, 907, 913, and 915 may correspond to operations 701, 703, 705, 709, and 711 of FIG. 7 respectively, overlapping descriptions are omitted below.

In operation 901, an exercise assisting application may be executed in response to a user input. Furthermore, a departure point at which an exercise is started and a destination at which the exercise is finished may be specified in the exercise assisting application.

In operation 903, a triggering condition for the automatic display of exercise state information is determined based on user input that is received by the electronic device. That is, the automatic notification may be set so that the exercise assisting method based on an exercise parameter may be performed. In some implementations, the user input may specify one or more of an exercise parameter, and a threshold value for the exercise parameter which when reached by the exercise parameter causes the electronic device to automatically output exercise state information (e.g., the value of the exercise parameter). For example, the exercise parameter may be any one of an exercise duration time, a moving distance, a moving speed, and consumed calories of the user. In some implementations, a predetermined sequence of threshold values for the exercise parameter may be determined, based on the user input, which when reached by the exercise parameter cause the electronic device to automatically output exercise state information.

In operation 905, the user begins exercising and the exercise assisting application begins monitoring the user's exercise.

In operation 907, the electronic device 100 may display a lock screen that includes information provided (e.g., generated) by the exercise assisting application.

In operation 909, the electronic device 100 may monitor the exercise parameter set in operation 903 in real-time based on various information collected by a sensor module.

In operation 911, the electronic device 100 may determine whether the value of the monitored exercise parameter reaches a specified threshold value. If the value of the monitored exercise parameter reaches the threshold value (e.g., a threshold value specified by the user in operation 903 and/or a threshold value determined based on user input received at operation 903), the process may proceed to operation 913, or, if the value of the monitored exercise parameter does not reach the predetermined value, the process may return to operation 907.

In operation 913, when the value of the monitored exercise parameter reaches the predetermined value, the electronic device 100 may generate an audio signal indicating an exercise state of the user. As discussed above, the audio signal may indicate the value(s) of one or more exercise parameters which at least in part constitute the exercise state of the user. The audio signal may correspond to the exercise parameter set in operation 903. Therefore, exercise state information implemented as the audio signal may vary with the exercise parameter set in operation 903 (e.g., see Table 1).

In operation 915, the electronic device 100 or the audio device 200A or 200B connected to the electronic device 100 may convert the audio signal generated in operation 913 into an acoustic vibration and may provide the acoustic vibration to the user.

In operation 917, the electronic device 100 may determine whether the user arrives at the destination based on the location information. If the user arrives at the destination, the process may be terminated, or, if the user does not arrive at the destination, the process may return to operation 907.

According to the exercise assisting method based on an exercise parameter according to an embodiment of the present disclosure, the user may be automatically provided with the exercise state information every time the value of the exercise parameter reaches the predetermined value. Furthermore, since the exercise state information may vary with the value of the exercise parameter, the user may be provided with the exercise state information optimized for the set exercise parameter.

The module or program module according to various embodiments of the present disclosure may include at least one of the above-mentioned elements, or some elements may be omitted or other additional elements may be added. Operations performed by the module, the program module or other elements according to various embodiments of the present disclosure may be performed in a sequential, parallel, iterative or heuristic way. Furthermore, some operations may be performed in another order or may be omitted, or other operations may be added.

According to an exercise assisting method according to an embodiment of the present disclosure, for example, the user may be acoustically provided with information on the exercise state of the user by providing a simple user input while jogging. Therefore, the user who is taking exercise may not have to stop exercising in order to manipulate an electronic device, and may thus concentrate on exercise.

FIGS. 1-9 are provided as an example only. At least some of the operations discussed with respect to these figures can be performed concurrently, performed in different order, and/or altogether omitted. It will be understood that the provision of the examples described herein, as well as clauses phrased as "such as," "e.g.", "including", "in some aspects," "in some implementations," and the like should not be interpreted as limiting the claimed subject matter to the specific examples. For example, and without limitation, it will be further understood, that the phrase "audio signal indicating the value of exercise parameter" may refer to any suitable type of signal that is generated based on the exercise parameter's value, such as a signal that identifies the value of the exercise parameter, a signal that indicates a range to which the value of the exercise parameter, a signal indicating whether a particular exercise goal is achieved based on the exercise parameter, etc. Furthermore, it will be understood that a lock screen of a device may be considered to be active when the device is locked, regardless of whether the lock screen is currently displayed. For example, the lock screen may be considered to be active when the lock screen is displayed or when the device is locked and transitioned into a standby mode in which the device's display is turned off.

The above-described aspects of the present disclosure can be implemented in hardware, firmware or via the execution of software or computer code that can be stored in a recording medium such as a CD-ROM, a Digital Versatile Disc (DVD), a magnetic tape, a RAM, a floppy disk, a hard disk, or a magneto-optical disk or computer code downloaded over a network originally stored on a remote recording medium or a non-transitory machine-readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. Any of the functions and steps provided in the Figures may be implemented in hardware, software or a combination of both and may be performed in whole or in part within the programmed instructions of a computer. No claim element herein is to be construed under the provisions of 35 U.S.C. 112, sixth paragraph, unless the element is expressly recited using the phrase "means for".

While the present disclosure has been particularly shown and described with reference to the examples provided therein, it will be understood by those skilled in the art that various changes in form and details may be made therein without departing from the spirit and scope of the present disclosure as defined by the appended claims.

What is claimed is:

1. An electronic device comprising:
   a memory;
   a display;
   at least one sensor including a GPS module; and
   at least one processor operatively coupled to the memory, configured to:
   execute an exercise assisting application;
   monitor exercise parameters by the at least one sensor;
   control the display to display a lock screen including information provided by the exercise assisting application;
   receive a plurality of inputs via the display requesting information on the monitored exercise parameters while the lock screen is active;
   in response to receiving each of the inputs, generate and output a first audio signal containing information on the exercise parameters;
   calculate an audio notification period based on intervals of time elapsed between each of the plurality of inputs provided on the lock screen; and
   automatically generate and output a second audio signal containing the information on the exercise parameters continually at the calculated audio notification period after the inputs are received until the completion of the exercise,
   wherein the exercise parameters includes at least one of an exercise duration time, a moving distance, an altitude, a moving speed, a distance to a destination, consumed calories, and a time taken to travel a predetermined distance.

2. The electronic device of claim 1, wherein the plurality of inputs include a touch that is performed in the lock screen.

3. The electronic device of claim 1, wherein the information provided by the exercise assisting application includes respective values of one or more exercise parameters that are selected in the exercise assisting application.

4. A method comprising:
   executing, by at least one processor of an electronic device, an exercise assisting application;
   monitoring, by at least one sensor of the electronic device, exercise parameters, wherein the at least one sensor includes a GPS sensor;
   displaying, on a display of the electronic device, a lock screen including information provided by the exercise assisting application;
   receiving a plurality of inputs via the display requesting information on the monitored exercise parameters while the lock screen is active;
   in response to receiving each of the inputs, generating and outputting, by the at least one processor, a first audio signal containing information on the exercise parameters;
   calculating, by the at least one processor, an audio notification period based on intervals of time elapsed between each of the plurality of inputs provided on the lock screen; and
   automatically generating and outputting, by the at least one processor, a second audio signal containing the information on the exercise parameters continually at the calculated audio notification period after the inputs are received until the completion of the exercise,
   wherein the exercise parameters includes at least one of an exercise duration time, a moving distance, an altitude, a moving speed, a distance to a destination, consumed calories, and a time taken to travel a predetermined distance.

5. The method of claim 4, wherein the inputs include a touch that is performed in the lock screen.

6. A non-transitory computer-readable storage medium storing one or more programs comprising instructions which, when executed by at least one processor of an electronic device cause the at least one processor to execute a method comprising the steps of:
   executing an exercise assisting application;
   monitoring, by at least one sensor of the electronic device, exercise parameters, wherein the at least one sensor includes a GPS sensor;
   displaying, on a display of the electronic device, a lock screen including information provided by the exercise assisting application;
   receiving a plurality of inputs via the display requesting information on the monitored exercise parameters while the lock screen is active;
   in response to receiving each of the inputs, generating and outputting a first audio signal containing information on the exercise parameters;
   calculating an audio notification period based on intervals of time elapsed between each of the plurality of inputs provided on the lock screen; and
   automatically generating and outputting a second audio signal containing the information on the exercise parameters continually at the calculated audio notification period after the inputs are received until the completion of the exercise,
   wherein the exercise parameters includes at least one of an exercise duration time, a moving distance, an altitude, a moving speed, a distance to a destination, consumed calories, and a time taken to travel a predetermined distance.

* * * * *